(12) United States Patent
Litvak et al.

(10) Patent No.: US 7,171,261 B1
(45) Date of Patent: Jan. 30, 2007

(54) FORWARD MASKING METHOD FOR ESTIMATING NEURAL RESPONSE

(75) Inventors: Leonid M Litvak, Los Angeles, CA (US); Edward H Overstreet, Valencia, CA (US)

(73) Assignee: Advanced Bionics Corporation, Valencia, CA (US)

( * ) Notice: Subject to any disclaimer, the term of this patent is extended or adjusted under 35 U.S.C. 154(b) by 580 days.

(21) Appl. No.: 10/741,410

(22) Filed: Dec. 19, 2003

Related U.S. Application Data

(60) Provisional application No. 60/435,376, filed on Dec. 20, 2002.

(51) Int. Cl.
*A61B 5/04* (2006.01)

(52) U.S. Cl. .................................... 600/544
(58) Field of Classification Search ................. 600/544
See application file for complete search history.

(56) References Cited

U.S. PATENT DOCUMENTS

| | | | |
|---|---|---|---|
| 3,751,605 A | 8/1973 | Michelson | |
| 4,400,590 A | 8/1983 | Michelson | |
| 4,495,384 A | 1/1985 | Scott et al. | |
| 5,143,081 A * | 9/1992 | Young et al. | 600/554 |
| 5,603,726 A | 2/1997 | Schulman et al. | |
| 5,626,629 A | 5/1997 | Faltys et al. | |
| 5,938,691 A | 8/1999 | Schulman et al. | |
| 6,067,474 A | 5/2000 | Schulman et al. | |
| 6,078,838 A * | 6/2000 | Rubinstein | 607/55 |
| 6,157,861 A | 12/2000 | Faltys et al. | |
| 6,195,585 B1 | 2/2001 | Karunasiri et al. | |
| 6,205,360 B1 * | 3/2001 | Carter et al. | 607/57 |
| 6,219,580 B1 | 4/2001 | Faltys et al. | |
| 6,249,704 B1 | 6/2001 | Maltan et al. | |
| 6,289,247 B1 | 9/2001 | Faltys et al. | |
| 6,295,467 B1 | 9/2001 | Kollmeier et al. | |
| 6,415,185 B1 | 7/2002 | Maltan | |
| 6,917,832 B2 * | 7/2005 | Hutten et al. | 607/28 |

FOREIGN PATENT DOCUMENTS

WO    WO-03/015863 A2    2/2003

OTHER PUBLICATIONS

Rubinstein et al., "The Neurophysiological Effects of Simulated Auditory Prosthesis Simulation" Second Quarterly Progress Report NO1-DC-6-2111.

(Continued)

*Primary Examiner*—Charles A. Marmor, II
*Assistant Examiner*—Zoe Baxter
(74) *Attorney, Agent, or Firm*—Philip H. Lee

(57) ABSTRACT

An improved forward-masking method of recording and processing neural responses ("NR") is provided, wherein the method does not assume a linear system response and does not assume a linear response at the interface between electrodes and tissue. The method of the present invention cancels out non-linearities and/or system hysteresis. Other artifacts such as system cross-talk between stimulation and recording circuits are also canceled out.

18 Claims, 6 Drawing Sheets

OTHER PUBLICATIONS van Wieringen, et al., "Comparison of Procedures to Determine Electrical Stimulation Thresholds in Cochlear Implant Users", Ear and Hearing, vol. 22(6), (2001), pp. 528-538.

Overstreet and Faltys inventors for AB-254U; U.S. Appl. No. 10/218,645, filed Aug. 13, 2002; entitled "Cochlear Implant and Simplified Method for Fitting Same".

Faltys inventor for AB-257U; U.S. Appl. No. 10/218,616, filed Aug. 13, 2002; entitled "Bionic Ear Programming System".

Segel, Overstreet, Kruger, and Mishra inventors for AB-313U; U.S. Appl. No. 10/651,653, filed Aug. 29, 2003; entitled "System and Method for Fitting a Cochlear Implant Sound Processor Using Alternative Signals".

Overstreet inventor for AB-362U; U.S. Appl. No. 10/647,372, filed Aug. 25, 2003; entitled "Enhanced Methods for Determining Iso-Loudness Contours for Fitting Cochlear Implant Sound Processors".

Maltan, Miller, and Harrison inventors for AB-376U; U.S. Appl. No. 10/662,615, filed Sep. 30, 2003; entitled "Cochlear Implant Sound Processor with Permanently Integrated Replenishable Power Source".

Overstreet, Litvak, and Faltys inventors for AB-378U; U.S. Appl. No. 10/698,097, filed Oct. 31, 2003; entitled "Multi-Electrode Stimulation to Elicit Electrically-Evoked Compound Action Potential."

Overstreet inventor for AB-379U; U.S. Appl. No. 10/698,098, filed Oct. 31, 2003; entitled "Method and System for Generating a Cochlear Implant Program Using Multi-Electrode Stimulation to Elicit the Electrically-Evoked Compound Action Potential".

Zeng, et al., "Loudness of Simple and Complex Stimuli in Electric Hearing", Annals of Otology, Rhinology & Laryngology, vol. 104 (9), pp. 235-238.

* cited by examiner

FORWARD MASKING METHOD FOR ESTIMATING NEURAL RESPONSE

The present application claims the benefit of U.S. Provisional Patent Application Ser. No. 60/435,376, filed 20 Dec. 2002, which application is herein incorporated by reference in its entirety.

BACKGROUND OF THE INVENTION

The present invention relates to methods of recording a neural response following stimulation of neural tissue. More specifically, the present invention relates to methods for measuring and processing neural responses that minimize stimulus artifacts and system noise.

Modern neural stimulators have the capability of measuring the effectiveness of electrical stimulation of a nerve tissue. This involves delivering a stimulus to a nerve through a stimulating electrode and recording the electrical response, as the nerve depolarizes and repolarizes, using a recording electrode. Such recording and capturing of nerve electrical activity is termed neural response imaging ("NRI").

Obtaining such a neural response ("NR") is important clinically for determining whether stimulation of nerves is occurring at a given stimulus setting and also for determining optimal stimulation parameters for each electrode or electrode configuration.

High quality responses are often difficult to obtain because the neural recordings can be marred by the presence of stimulus artifacts, i.e., the neural recording records the voltage potential of the stimulus pulse and may obscure the desired NR signal. Another source of recording artifact is cross-talk between the recording circuit and the stimulation circuit. When the recording system is built into a small implantable system, such as an implantable cochear stimulator or a spinal cord stimulator, the stimulation and recording circuits are necessarily placed very close to each other within the stimulator and, hence, cross-talk can develop between the two circuits.

One method of reducing the stimulus artifact and cross-talk and extracting an NR is to use a forward masking technique. Unfortunately, the conventional forward masking paradigm often leaves large residual artifacts, because the paradigm assumes linearity and non-hysteresis of the system response. The hysteresis leads to a response to the probe following the masker to have an artifact which is different from the response to the probe alone, resulting in a residual artifact.

Accordingly, what is needed is an improved method of recording and processing neural responses, which method is not dependent on system linearity.

SUMMARY OF THE INVENTION

The present invention addresses the above and other needs by providing an improved NR recording and data processing method.

In one aspect of the invention, there is provided a method of recording and estimating a neural response, NR, using a stimulating electrode and a recording electrode, the method comprising:

(a) recording a first response, Rmp_distant, while a first supra-threshold stimulus pulse, S1, is delivered to a target nerve and, thereafter, a second stimulus pulse, S2, is delivered to the target nerve, wherein S2 is initiated outside of the relative refractory period of the action potential elicited by delivery of S1;

(b) recording a second response, Rmp, while a supra-threshold stimulus pulse, S3, which is essentially identical to S1, is delivered to the target nerve, and a second stimulus pulse, S4, essentially identical to S2 is delivered to the target nerve, wherein S4 is initiated within the relative refractory period of the action potential of the target nerve elicited by delivery of S3;

(c) recording a third response, Rm, while a supra-threshold stimulus pulse, S5, essentially identical to S1, is delivered to the target nerve; and (d) processing the recordings to yield an estimate NR in accordance with the relation: estimated NR=(Rmp_distant−Rm)−Time Shift (Rmp−Rm), wherein the Time Shift fits the response in time such that the relevant response peaks line up.

It is a feature of the present invention to provide a recording and processing method that can accommodate hysteresis of response at the electrode-tissue interface.

It is a further feature of the invention to provide a method which allows recording and processing of NR with minimal system modifications to existing recording systems by processing the recordings differently rather than by making wholesale hardware changes to the recording system.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
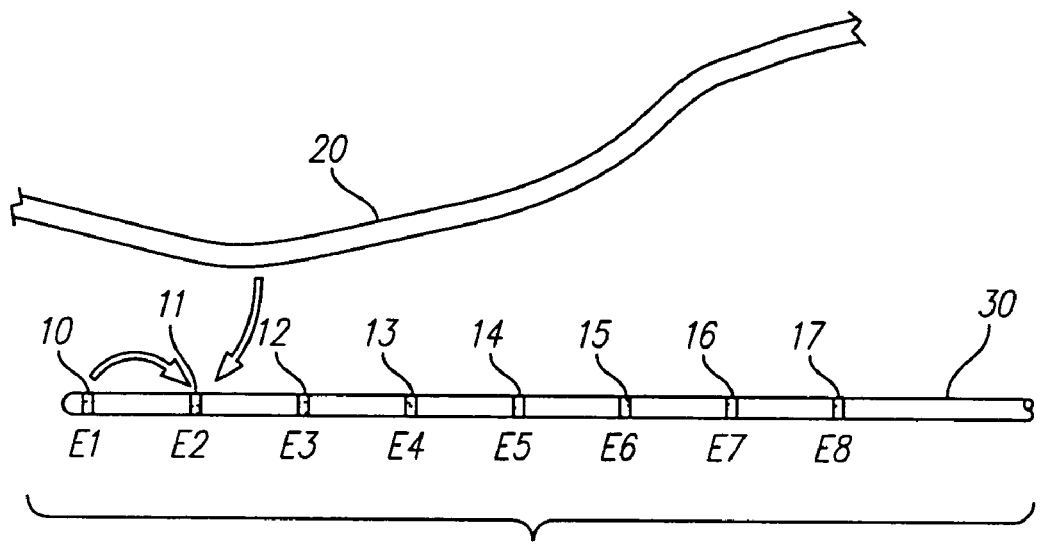
FIG. 1A shows an electrode array used to stimulate a target nerve, which electrode array can have both a stimulating and a recording electrode.

FIG. 1A shows a generic lead 30 having an electrode array with electrodes E1 . . . E8, numbered 10–17, respectively, and which may be used with the method of the present invention. The lead 30 can be attached to an implantable pulse generator ("IPG") (not shown). The IPG may provide independently controllable stimuli to each of the electrodes, 10–17. In addition, the circuitry in the IPG that is attached to each electrode E1 . . . E8 can be switched between stimulation mode and recording mode. As one example, electrode 10 may be a selected as a stimulating electrode with the IPG housing serving as a return or indifferent electrode to complete the circuit. When the IPG housing is used as an electrode, that represents monopolar stimulation. On the other hand, if the return electrode is another electrode in the electrode array, that represents a bipolar electrode configuration. Electrode 11 may be selected as a recording electrode, forming a part of the recording circuit, wherein electrode 11 can record an electrical stimulus delivered from electrode 10 as well as electrical activity, e.g., a nerve action potential, along nerve 20. The recorded electrical stimulus is termed a "stimulus artifact," whereas the recorded electrical activity along the nerve or the nerve action potential, is the neural response or "NR". In most cases the electrical stimulus (artifact) recorded is very large compared to the action potential (desired NR) and may obscure the action potential, and therefore a method is needed to filter out the dominating artifact.

Figure 1B:
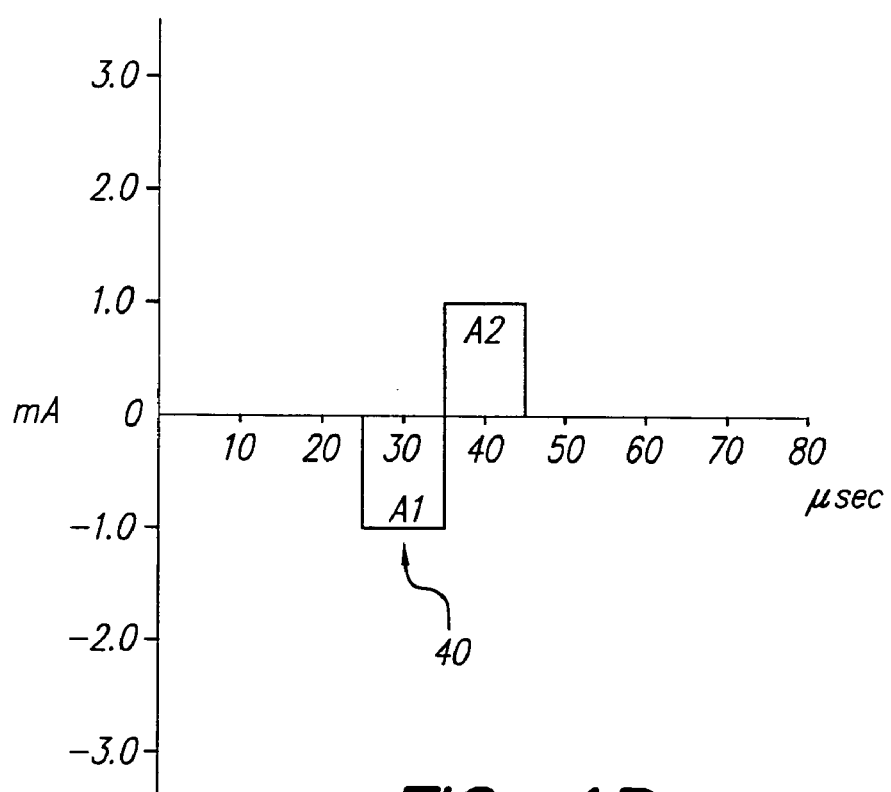
FIG. 1B shows a charged-balanced, biphasic stimulus pulse that can be used to stimulate a nerve.

FIG. 1B shows one example of a biphasic stimulus that may be delivered through electrode 10. The stimulus 40 can consist of two parts, a negative first phase having area A1 and a positive phase having area A2. It is usually the negative phase that causes nerve tissue to depolarize (fire). The stimulus 40 shown is "charged balanced" because the negative area within curve A1 is equal to the positive area A2. While the depolarization of nerve is generally initiated only by the negative phase of a stimulus, a biphasic, charge-balanced stimulus is often employed because such charge balancing helps reduce electrode corrosion and build-up of charges which can harm surrounding tissue.

When the amplitude and pulsewidth of the stimulus 40 is supra-threshold (a stimulus large enough to depolarize a target nerve), the voltage gradient at some surface point on the nerve 20 will be sufficiently negative as to cause the nerve to depolarize from its resting state and propogate an electrical signal along the length of the nerve. The voltage gradient of this electrical signal propagation can be captured as an NR using the recording electrode 11.

Before discussing the present method of obtaining NRs, it is helpful to understand the components of two exemplary stimulation systems in which the present method for obtaining NRs can be employed.

Figure 1C:
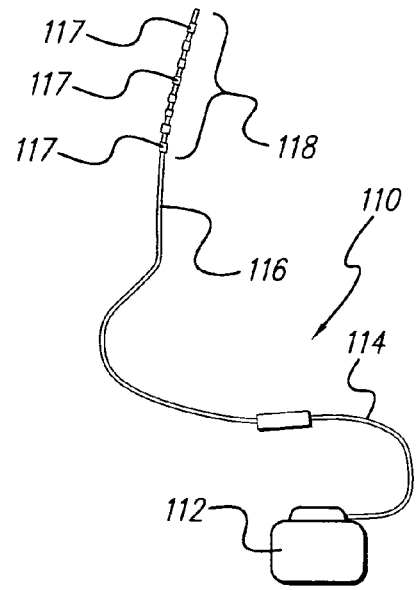
FIG. 1C shows an exemplary stimulation system that may be used to perform spinal cord stimulation (SCS)
Figure 1D:
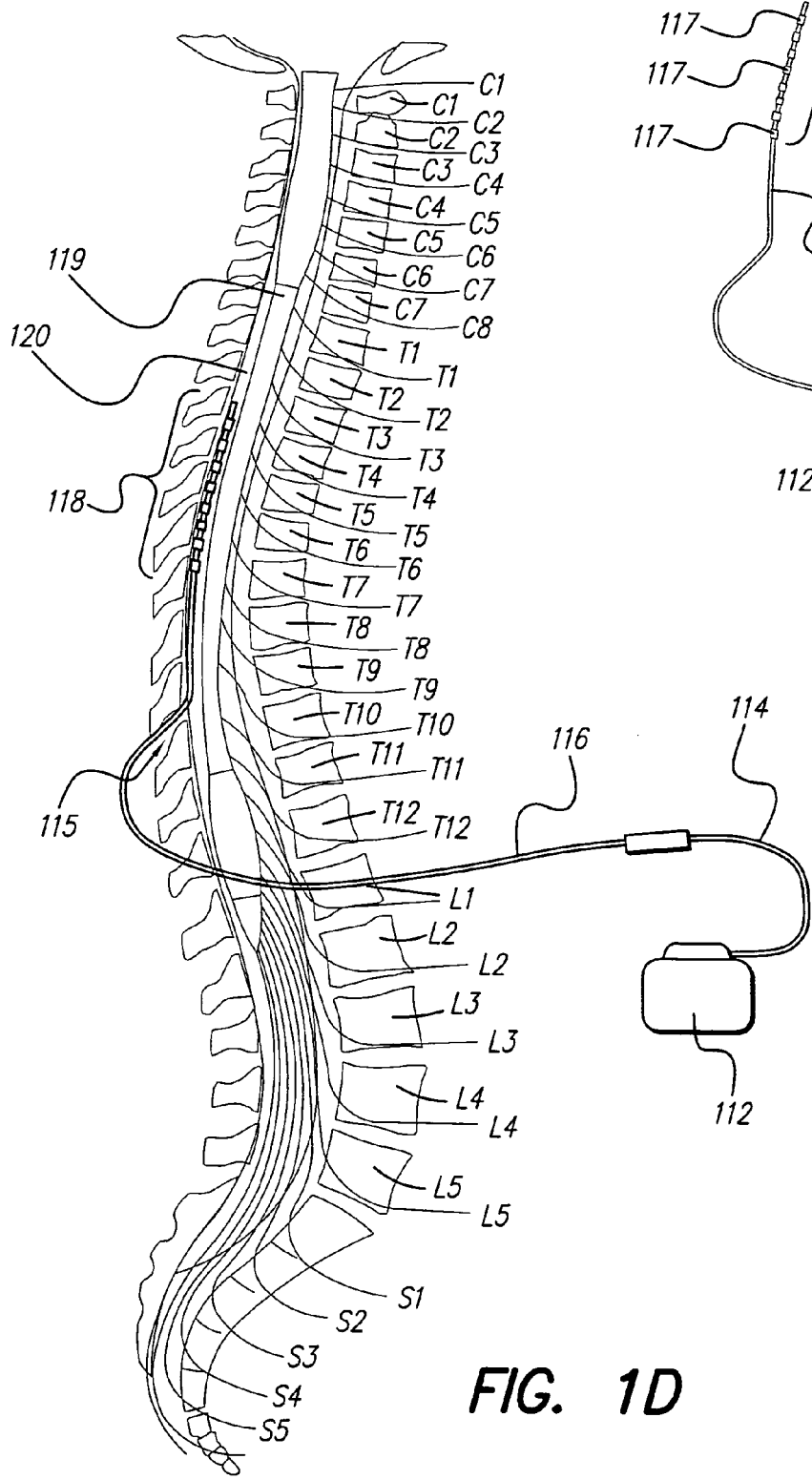
FIG. 1D shows the system of FIG. 1C with the electrode array implanted for stimulating spinal cord nerves.

FIGS. 1C and 1D show an exemplary stimulation system 110 that may be used as a spinal cord stimulator (SCS) system for treating chronic pain. In such an application, the lead 116 and, more particularly, the electrode array 118 can be implanted in the epidural space 120 of a patient to be in close proximity to the spinal cord 119.

The system 110 typically comprises an implantable pulse generator (IPG) 112, an optional lead extension 114, an electrode lead 116, having an electrode array 118. The electrode array 118 includes a plurality of electrode contacts 117 (also referred loosely as "electrodes"). The electrode contacts 117 can be arranged, for example, in an in-line array 118 near the distal end of the lead 116. Other electrode array configurations may also be used. The IPG 112 can generate stimulation current pulses that are applied to selected ones of electrodes 117 within the electrode array 118.

A proximal end of the lead extension 114 can be removably connected to the IPG 112 and a distal end of the lead extension 114 can be removably connected to a proximal end of the electrode lead 116. The electrode array 118 is formed on a distal end of the electrode lead 116. The in-series combination of the lead extension 114 and electrode lead 116 carry the stimulation current from the IPG 112 to electrodes of the electrode array 118. The lead extension 114 need not always be used with the neural stimulation system 110, but may be used when the physical distance between the IPG 112 and the electrode array 118 requires its use. Because of the lack of space near the lead exit point 115 where the electrode lead 116 exits the spinal column, the IPG 112 is generally implanted in the abdomen or above the buttocks. The lead extension 114 facilitates locating the IPG 112 away from the lead exit point 115. A more complete description of an SCS system may be found in U.S. Pat. No. 6,516,227, which patent is incorporated herein by reference in its entirety.

It is noted that the SCS system comprising a lead 116, with electrode array 118 connected to an implantable pulse generator (IPG) 112 is a typical set of components for many stimulation systems for treating various ailments. For example, in deep brain stimulation to treat Parkinson's Disease, a system can include those basic components: an IPG, a lead and at least one electrode contact on the lead for delivering stimuli to a target nerve. An external device which is not implanted, e.g., a device programmer, can be used to communicate transcutaneously (through the skin) with the implanted IPG.

Figure 1E:
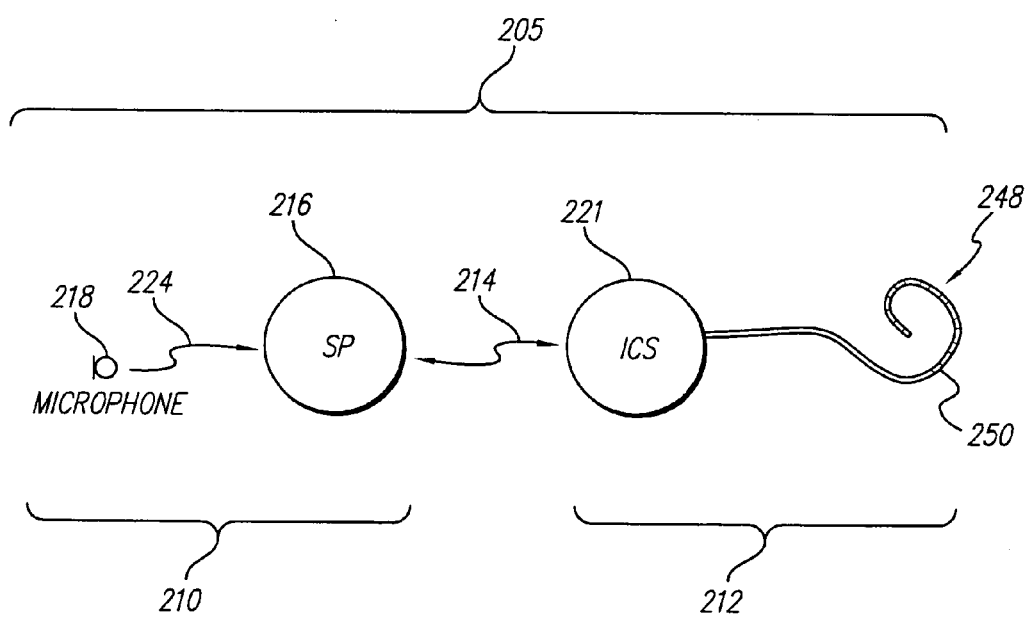
FIG. 1E shows a diagrammatic representation of a cochlear implant system that includes an external speech processor, SP, and an implanted cochlear stimulator (ICS)

FIG. 1E shows another exemplary stimulation system which is a cochlear system that can include an external component and an implantable component. FIG. 1E shows a cochlear stimulation system 205 that includes a speech processor portion 210 and a cochlear stimulation portion 212. The speech processor portion 210 includes a speech processor (SP) 216 and a microphone 218. The microphone 218 may be connected directly to the SP 216 or coupled to the SP 216 through an appropriate communication link 224. The cochlear stimulation portion 212 includes an implantable cochlear stimulator (ICS) 221 and an electrode array 248. The electrode array 248 is adapted to be inserted within the cochlea of a patient. The array 248 includes a plurality of electrodes 250, e.g., sixteen electrodes, spaced along the array length and which electrodes are selectively connected to the ICS 221. The electrode array 248 may be substantially as shown and described in U.S. Pat. No. 4,819,647 or 6,129,753, both patents incorporated herein by reference. Electronic circuitry within the ICS 221 allows a specified stimulation current to be applied to selected pairs or groups of the individual electrodes included within the electrode array 248 in accordance with a specified stimulation pattern defined by the SP 216.

The ICS 221 and the SP 216 are shown in FIG. 1E as being linked together electronically through a suitable data or communications link 214. In some cochlear implant systems, the SP 216 and microphone 218 comprise the external portion of the cochlear implant system and the ICS 221 and electrode array 248 comprise the implantable portion of the system. Thus, the data link 214 is a transcutaneous (through the skin) data link that allows data, power and control signals to be sent from the SP 216 to the ICS 221. In some embodiments, data and status signals may also be sent from the ICS 221 to the SP 216.

In many systems that stimulate nerve or nerves using an electrical pulse stimulus, it may be desirable to quickly determine the neural response (NR) of a nerve or nerves in response to an applied stimulus. Such a determination of NR, when performed quickly and accurately, can facilitate the optimal setting of the stimulus parameters, e.g, current amplitude and pulsewidth and, moreover, can help characterize the response characteristic of a nerve to various applied stimulus levels. Such information may be useful for setting the upper and lower boundaries of acceptable stimulation levels.

Figure 2:
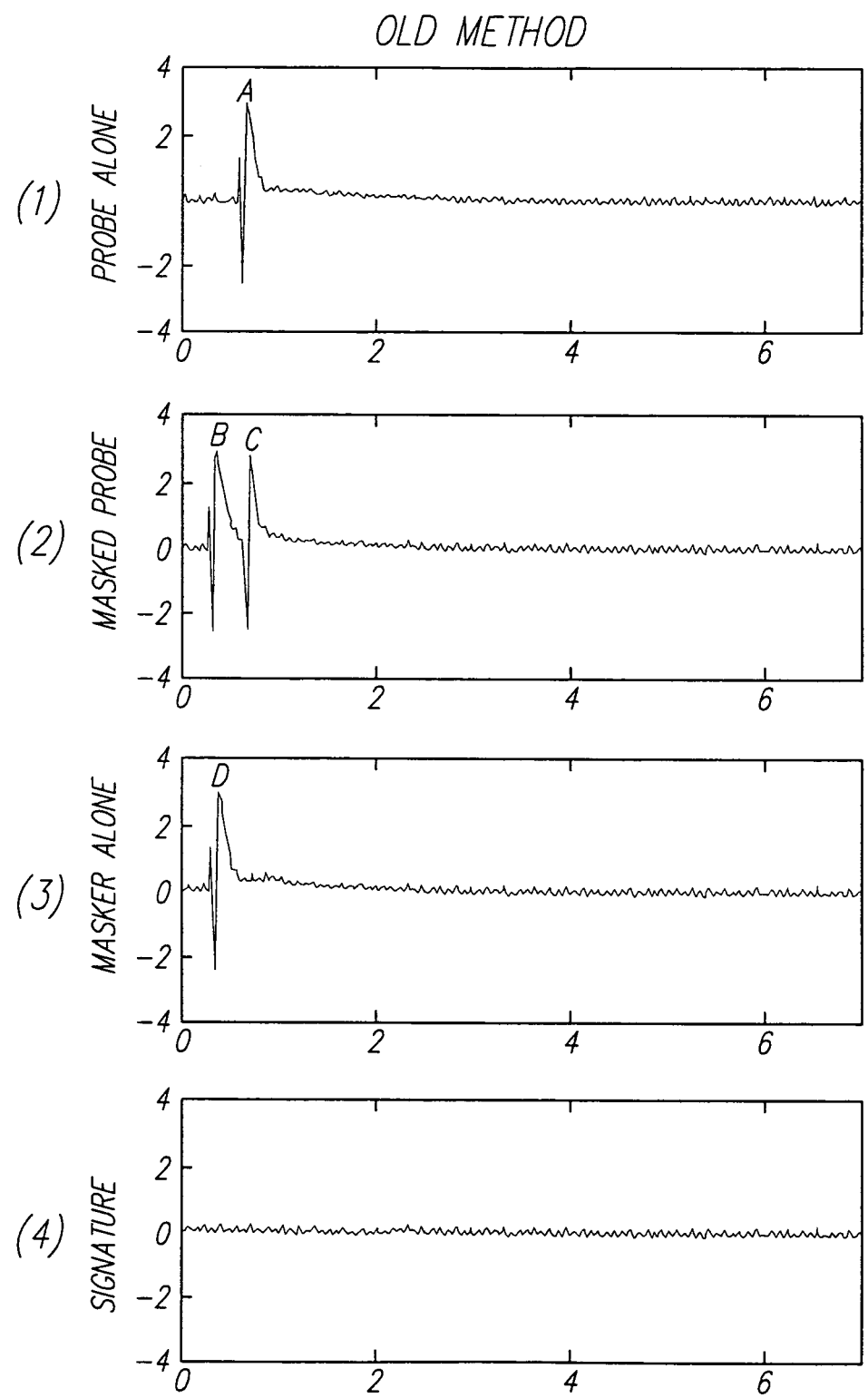
FIG. 2 shows a representation of the conventionally practiced forward masking method.
Figure 3:
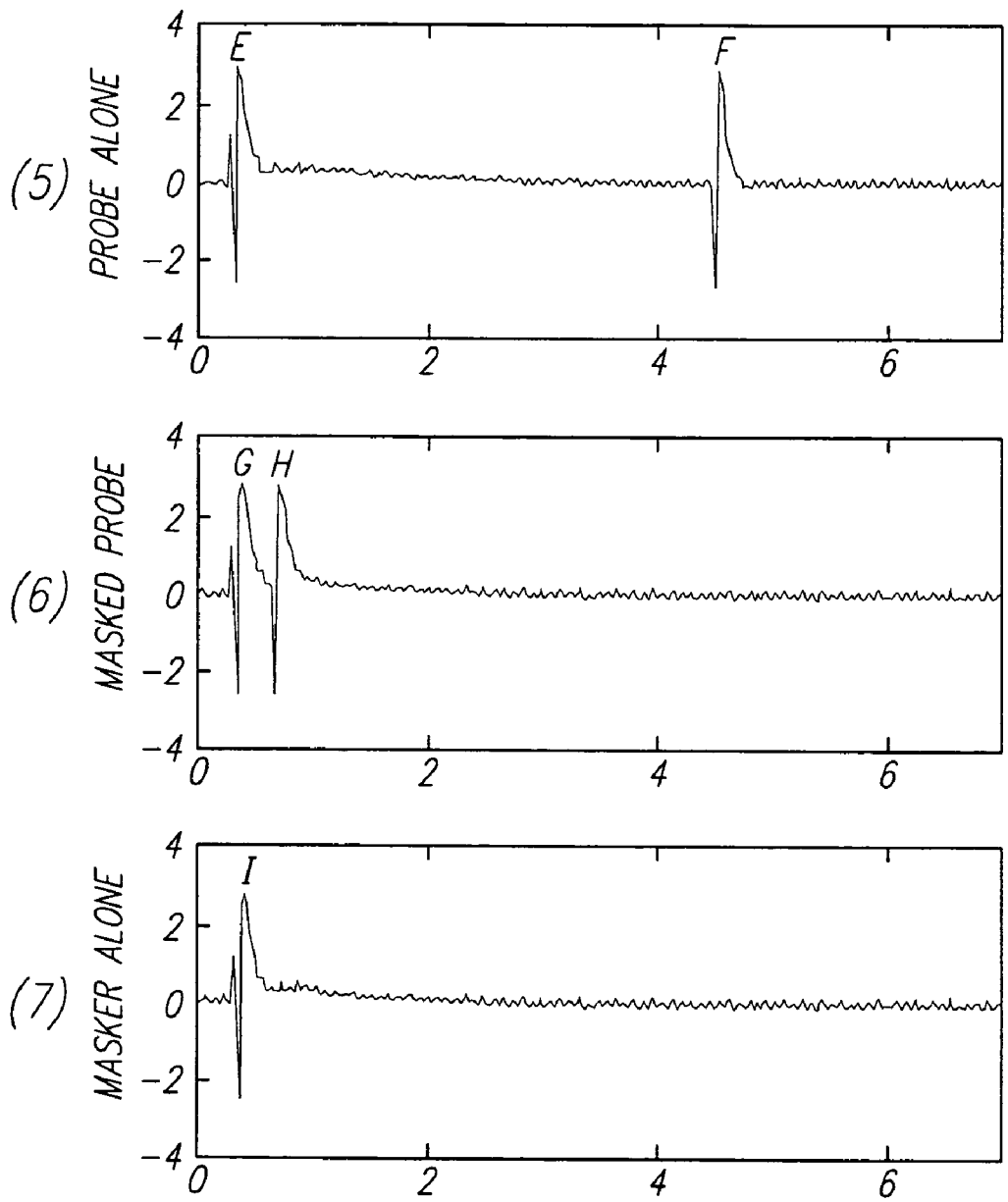
FIG. 3 shows, in accordance with the present invention, the method which does not assume linearity at the electrode-tissue interface.

FIGS. 2 and 3 show various response recordings which show stimulus artifacts and neural responses (NRs). The X-axes of the plots are in milliseconds and the Y-axes are in milliamperes. The amplitude of the recorded NR is generally much smaller than that of the stimulus response. The recorded stimulus response or the stimulus artifact, swamps the desired NR, as shown in the peaks B, D, E, G and 1. A recording electrode, for example, electrode 11 (E2) shown in FIG. 1A, can record both the stimulus artifact and the NR in peaks B, D, E, G and 1, and it is therefore necessary to extract the NR from artifacts and noise.

FIG. 2 shows the sequence of recordings, as conventionally practiced, using a forward masking paradigm. In this example, it is assumed that one electrode, for instance, electrode 10 (E1), as seen in FIG. 1A, delivers a stimulus and one electrode, e.g., electrode 11 (E2), can be the recording electrode.

Recording is activated during the entire time that one or more stimulus pulses are delivered. Four responses can be recorded:

1. plot (1), a response to the stimulus pulse, which is termed a probe response, Rp;

2. plot (2), a response to a first stimulus "the masker", followed by a second stimulus pulse, "the probe", which total recorded response is labeled Rmp (response of the masker-probe);

3. plot (3), a response Rm to a stimulus is labeled "masker alone," which is the total recorded response; and 4. plot (4), a response R0 (a signature response) which is the response to no stimulation.

R0 includes system noise from cross-talk and system offset. Each of these recorded responses Rp, Rmp, Rm and R0 are obtained in separate (not simultaneous) recordings and can be stored in a database, for example, in memory or other digital or analog storage medium to be recalled later for further data processing to obtain an estimate of NR.

An estimate of NR is obtained by applying the formula Rp−(Rmp−Rm)−R0. In FIG. 2, plot (1) shows peak A, which represents Rp=stimulus artifact+NR+system offset/noise. Plot (2) at peak B, represents Rmp=Stimulus artifact+NR+system offset/noise. At peak B, the stimulus applied through electrode 10 is supra-threshold, i.e., the stimulus has sufficient amplitude and pulsewidth to cause the nerve 20 to fire. Second peak C, represents Rmp=stimulus artifact+system offset/noise. This second peak C does not include NR because it is within the relative refractory period of the nerve in which period the nerve cannot be further elicited to fire because the nerve is in a recovery stage. Peak D in plot (3) represents Rm=stimulus artifact+NR+system offset/noise. Plot (4) represents R0 (the "signature") which is the system offset/noise over a specific duration of recording time.

As seen in FIG. 2 the X-axis of each plot represents time in milliseconds. The specific example in FIG. 2 depicts a recording duration of about 7 milliseconds. It is understood that the 7 milliseconds is only an example duration and other recording durations may be used.

It can be seen that when plot (2) is subtracted by plot (3), in other words (Rmp−Rm), the subtraction eliminates the first peak B, leaving only peak C. This subtraction also cancels system offset/noise present in both plot (2) and (3). Thus, the term (Rmp−Rm) theoretically leaves only the residual stimulus artifact. Further substituting into the expression Rp−(Rmp−Rm)−R0 yields plot (1)−stimulus artifact−plot (4) or (stimulus artifact+NR+system offset)−(stimulus artifact)−(system offset), which yields only NR, the estimate of the neural response.

This forward masking technique assumes that the time interval between the onset of the probe pulse, shown as peak B in FIG. 2, and the masker pulse, shown as peak C in FIG. 2, is smaller than the nerve refractory period, such that peak C, "masks out" the response to the peak B. The "nerve refractory period" is that period of time where a nerve, which has just been fired, cannot be fired again because the nerve is in a recovery stage.

Figure 4:
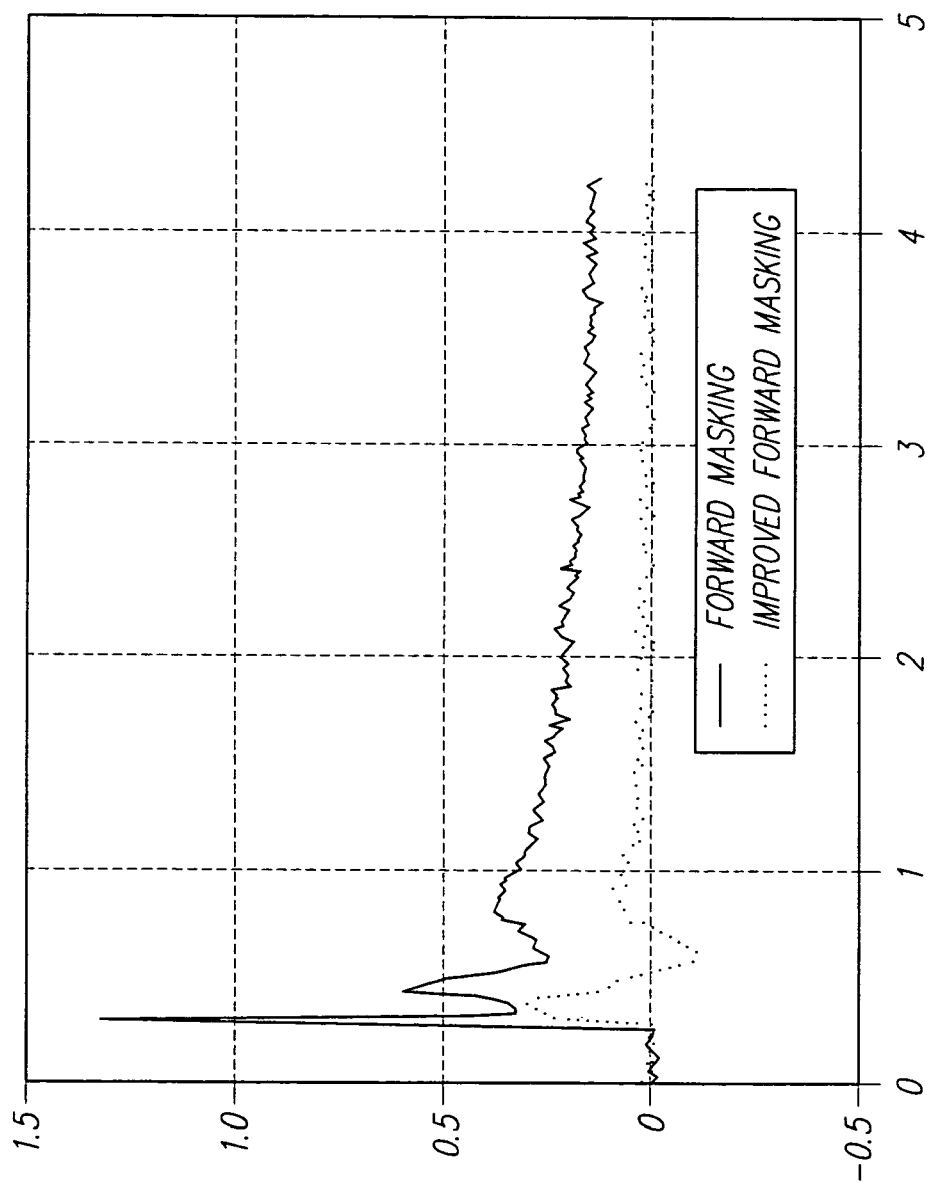
FIG. 4 shows the derived NR for the conventional forward-masking method compared to the improved forward-masking method of the present invention.

In practice, the conventional method outlined above can result in sizable residual artifacts in the neural responses, as shown in the solid line plot of FIG. 4. Some possible reasons why the method of cancellation is imperfect include the fact that the state of the system at the outset of the probe alone presentation differs from the state of the system during the probe presentation after the masker. Specifically, the state of the system during the time of peak C of plot (2) may not be the same as in peak A of plot (1) which means that the subtraction does not cancel the stimulus artifact as intended. Another reason is that internal capacitors and/or the electrode-fluid interface accumulate charge during the masker presentation (first peak B in plot (2)) and a further reason is that there are non-linearities and/or hysteresis present in the IPG circuits and the electrode-tissue interface. Peak C may include some state differences caused by non-linear system state changes after peak B. These non-linear effects are not accommodated in the conventional forward masking technique.

FIG. 3 shows, in accordance with the method of the present invention, a sequence of response recordings which provides an improved NR measurement method that is less sensitive to system non-linearities and hysteresis. Referring to FIG. 3, the method comprises: as shown in plot (5), obtaining a response where the masker (peak E) and the probe (peak F) are separated by a time gap that is greater than the relative refractory period of the stimulated nerve. The plot (5), which includes peaks E and F, is designated as Rmp_distant. Specifically, with cochlear nerve, the refractory period is about 3 milliseconds. The method further comprises, as shown in plot (6), obtaining the response to a masker-probe combination, Rmp, in which the first peak G is followed closely by second peak H within the relative refractory period of the stimulated nerve. Plot (7) is also obtained, which records the masker alone, Rm, shown as peak I.

The three recording plots (5), (6) and (7), or in other words, Rmp_distant, Rmp or Rm, respectively, may be obtained in any order. In fact to increase the accuracy of each plot, a multiple number of runs may be obtained to get averaged plots of at least one of Rmp_distant, Rmp or Rm. In general, the more runs that are performed for each recording, the more accurate the final estimated NR result can be. At some point, however, from a statistical standpoint, performing additional runs will not provide noticeable improvement to the accuracy. As a variation on the theme of averaging, the present method may be repeated in its entirety multiple times in order to obtain many estimated NRs and then, these can be averaged to provide an average NR which should be more accurate than a single estimated NR.

The stimulus applied to obtain peaks E, G and I should all be the same and should be supra-threshold stimuli. The stimulus applied to obtain F and H should also be the same, but sub-threshold, in order for the present method to work.

The NR can be estimated by applying the formula: (Rmp_distant−Rm)−Time Shift (Rmp−Rm), where Time Shift(Rmp−Rm) is a function that shifts the response in time such that the responses to the peaks F and H line up. (Rmp_distant−Rm) yields Rp, which is stimulus artifact+ NR, while system offset/noise cancels out. (Rmp−Rm) represents the stimulus artifact with no NR. Any system non-linearities are substracted out since such non-linearities presumably exist in both plot (6) and (7). Substituting for (Rmp_distant−Rm)−Time Shift (Rmp−Rm) therefore extracts out NR. Note that the method of the present invention does not assume system linearity or non-hysteresis.

Thus, in summary, the present invention provides a method of recording and processing neural response (NR) using a stimulating electrode and a recording electrode. The method can comprise: (a) recording Rmp_distant, while a first supra-threshold stimulus pulse, S1, is delivered to a target nerve and, thereafter, a second stimulus pulse, S2 is delivered to the target nerve, wherein S2 is initiated outside of the relative refractory period of the action potential elicited by delivery of S1; (b) recording Rmp, while a supra-threshold stimulus pulse, S3, which is essentially identical to S1, is delivered to the target nerve and a second stimulus pulse, S4, essentially identical to S2 is delivered to the target nerve, wherein S4 is initiated within the relative refractory period of the action potential of the target nerve elicited by delivery of S3; (c) recording Rm, while a supra-threshold stimulus pulse, S5, essentially identical to S1, is delivered to the target nerve; and (d) processing the recordings to yield an estimate NR in accordance with the relation: estimated NR=(Rmp_distant−Rm) Time Shift (Rmp−Rm).

In an embodiment of the present method, the target nerve that is stimulated and that produces an NR may be a cochlear nerve. In another embodiment of the present method, the target nerve may be a spinal cord nerve.

The stimulating electrode and recording electrode may be part of the same electrode array. Or, in some cases, the stimulating electrode and recording electrode may be located on different electrode arrays. For instance, spinal cord stimulation often uses two electrode arrays that are placed closely on either side of the midline. It may be possible that the recording electrode is selected on one electrode array while the stimulating electrode is located on the other electrode array.

While constant voltage stimulus may be used, the use of constant current stimulation is preferred as it is easier to control the quantity of current that is delivered, and as a constant current source, delivers the same current regardless of the specific impedance of the stimulus delivery system, e.g., the lead impedance and tissue/electrode contact interface impedance. In addition, while a uniphasic stimulus pulse may be used, the use of a biphasic, charged-balanced stimulus pulse is preferred, in accordance with the present method. In particular, such a biphasic stimulus, generally has a first phase which is of negative polarity and the second phase which is of positive polarity. As such, the stimulating electrode delivering a biphasic stimulus pulse is both cathodic and anodic depending on the pulse phase.

The method of the present invention may be employed in a variety of stimulation systems. The most common system is the exemplary system that includes an implantable pulse generator (IPG) or stimulator that is connected to a lead having at least one electrode contact or an array of electrode contacts. In such a system the electronic circuitry for sampling and recording Rmp, Rm and Rmp_distant, as well as calculating and processing the NR, may all be contained in the IPG or the implantable device. The implantable device can include sampling circuitry, memory for storing the sampled data, e.g., the Rmp, Rm and Rmp_distant, and a microprocessor for processing the recorded data. The estimated NR may then be used by the IPG or implantable device to automatically adjust or set stimulus parameters based on the NR. In addition, the estimated NR as well as recorded sampled data, Rmp, Rm and Rmp_distant, may be up-linked to an external device such as a device programmer which is not implanted. The device programmer and implanted device, e.g., IPG, can have a transcutaneous communications link such as an RF link, which link can be used to transmit control signals and data between the implanted and external devices.

In yet another embodiment, the method of the present invention may be used in a cochlear implant system which has both an ICS 221 (implanted component) and SP 216 (external device). The ICS and SP can be linked transcutaneously through a communications link such as a radio-frequency (RF) link. The SP device is commonly in the form of an external, behind-the-ear (BTE) device that is located behind the ear. In such a cochlear system, because of space limitations, the microprocessor which actually performs the NR calculation and estimation can be placed in the external BTE device rather than in the implanted ICS.

While the method of the present invention can record the various responses, Rmp_distant, Rmp and Rm, in an analog format, in general, in order to make calculations with a processor, the recordings can be converted to a digital format. However, continuous analog recording systems require too much space and therefore cannot be fully implanted into a small, implantable device. A sampling system, that takes discrete data samples over a specific duration, however, can be fully contained in an implantable device and also store the sampled recording data such as Rmp_distant, Rmp and Rm into memory, which may also be included in the implantable device. A processor or, more specifically, a microprocessor is preferably included, which is capable of performing numerical functions such as addition, subtraction, multiplication and division, among other common functions. By storing the sampled recordings as data arrays in memory, they may be easily manipulated by the microprocessor in order to carry out the present method for obtaining an estimated NR.

FIG. 4 shows that the NR obtained using the improved method of the present invention results in lower artifact, as shown by the dashed-line plot, because the state of the system during the onset of the probe is more similar between Rmp_distant and Rmp, compared to Rp and Rmp, which are in the conventional forward masking paradigm.

The example of the present method shown in FIG. 3 employs a response recording which is about 7 milliseconds long. Having data samples that are the same duration can facilitate manipulation and processing. However, shorter or longer recording durations among Rmp_distant, Rmp, and Rm can be used as long as the peaks E, F, G, H and I are captured. For ease of data processing, the entire plots may be subtracted from entire plots, e.g., all data points in plot (5) may be subtracted by plot (6). This is most easily performed using sets of data arrays and a processor. Alternatively, a smaller data window that includes each of the relevant peaks may be manipulated to obtain the same NR result. These are minor modifications to the method which fall within the scope of the present invention.

While the invention herein disclosed has been described by means of specific embodiments and applications thereof, numerous modifications and variations could be made thereto by those skilled in the art without departing from the scope of the invention set forth in the claims. A1

What is claimed is:

1. A method of recording and processing neural response (NR) using a stimulating electrode and a recording electrode, the method comprising:
   (a) recording a response in which the first stimulus and the second stimulus are separated by a time gap greater than the relative refractory period (Rmp_distant), while a first supra-threshold stimulus pulse, S1, is delivered to a target nerve and, thereafter, a second stimulus pulse, S2 is delivered to the target nerve, wherein S2 is initiated outside of the relative refractory period of the action potential elicited by delivery of S1;
   (b) recording a response in which a first stimulus and a second stimulus are separated by a time gap of less than the relative refractory period (Rmp), while a supra-threshold stimulus pulse, S3, which is essentially identical to S1, is delivered to the target nerve, and a second stimulus pulse, S4, essentially identical to S2 is delivered to the target nerve, wherein S4 is initiated within the relative refractory period of the action potential of the target nerve elicited by delivery of S3;
   (c) recording a stimulus pulse (Rm), while a supra-threshold stimulus pulse, S5, essentially identical to S1, is delivered to the target nerve; and
   (d) processing the recordings to yield an estimate NR in accordance with the relation: estimated NR=(Rmp_distant−Rm)−Time Shift(Rmp−Rm).

2. The method of claim 1, wherein each of the recordings is the same duration.

3. The method of claim 1, wherein S1 and S2 are essentially identical.

4. The method of claim 1, wherein the target nerve is a cochlear nerve.

5. The method of claim 1, wherein the stimulating electrode and recording electrode are part of an electrode array.

6. The method of claim 1, wherein the stimuli S1, S2, S3 and S4 are delivered in a monopolar mode.

7. The method of claim 1, wherein the target nerve is a spinal cord nerve.

8. The method of claim 1, wherein S1, S2, S3, S4, and S5 are all charged-balance, biphasic stimuli, the first phase of each stimuli having a negative polarity.

9. The method of claim 1, wherein S1, S2, S3, S4, and S5 are all current-controlled, constant-current stimuli.

10. The method of claim 1, wherein at least one of the steps (a), (b) or (c) is repeated in order to provide an averaged value of at least one of Rmp_distant, Rmp, or Rm, which averaged value is used in step (d).

11. The method of claim 1, further comprising:
   (e) repeating all of the steps (a), (b), (c) and (d) at least once and averaging the obtained value of all estimated NRs to obtained an averaged estimated NR.

12. The method of claim 1, wherein the step (d) processing the recording is accomplished by uploading Rmp_distant, Rmp and Rm from the implanted device to a microprocessor located in an implanted device, so that all processing is accomplished inside the implanted device.

13. The method of claim 12, wherein the implanted device is a spinal cord stimulator.

14. The method of claim 12, wherein the implanted device is an implanted cochlear stimulator.

15. The method of claim 1,
   wherein the step (d) processing the recording is accomplished by uploading the Rmp_distant; the Rmp and Rm from the implanted device and processing the recordings with a microprocessor that is located in an external device; and
   wherein the external device has a communications link with the implanted device.

16. The method of claim 15, wherein the external device is a behind-the-ear (BTE) device of a cochlear stimulator.

17. The method of claim 15, wherein the steps (a), (b) and (c) are accomplished by sampling and recording Rmp_distant, Rmp and Rm in digital form and storing them in a memory.

18. The method of claim 17, wherein the step (d) is performed by retrieving the digital recordings of Rmp_distant, Rmp and Rm from memory, and using a microprocessor capable of numerical functions such as adding and subtracting data points in data arrays, which functions may be used to calculate estimated NR.

* * * * *